United States Patent [19]

Farge et al.

[11] 4,261,993
[45] Apr. 14, 1981

[54] INDOLE DERIVATIVES

[75] Inventors: Daniel Farge, Thiais; Alain Jossin, St-Cloud; Gerard Ponsinet, Sucy-en-Brie; Daniel Reisdorf, Thiais, all of France

[73] Assignee: Rhone Poulenc Industries, Paris, France

[21] Appl. No.: 147,320

[22] Filed: May 6, 1980

[30] Foreign Application Priority Data

May 9, 1979 [FR] France ................... 79 11708

[51] Int. Cl.³ .......................... C07D 417/14; C07D/417/12; A61K/31/54
[52] U.S. Cl. ...................... 424/246; 544/32
[58] Field of Search ........... 424/246; 544/32

[56] References Cited

U.S. PATENT DOCUMENTS

| 4,188,482 | 2/1980 | Zinnes et al. | 544/32 |
| 4,189,480 | 2/1980 | Farge et al. | 544/32 |

*Primary Examiner*—John M. Ford
*Attorney, Agent, or Firm*—Stevens, Davis, Miller & Mosher

[57] ABSTRACT

Indole derivatives of the formula:

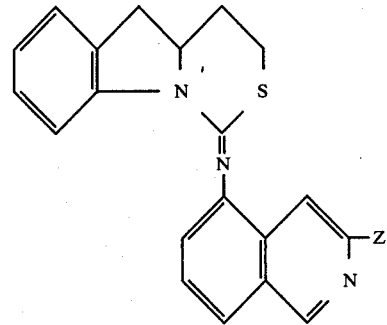

wherein Z represents hydrogen, alkyl of 1 through 10 carbon atoms, or alkoxyalkyl of the formula —(CH$_2$)$_n$—OR in which R represents alkyl of 1 through 8 carbon atoms and n represents 1 or 2, and their non-toxic pharmaceutically acceptable acid addition salts, are new compounds possessing useful pharmacological properties. They are particularly valuable as analgesic agents; some of them are also useful as anti-inflammatory and antipyretic agents.

7 Claims, No Drawings

INDOLE DERIVATIVES

This invention relates to new therapeutically useful indole derivatives, to processes for their preparation and pharmaceutical compositions containing them.

The new indole derivatives of the present invention are those compounds of the general formula:

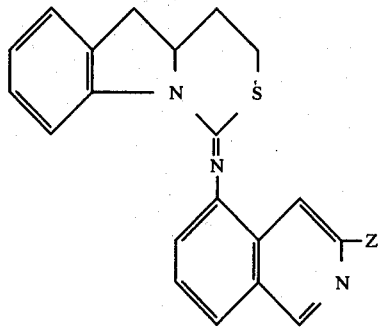

wherein Z represents a hydrogen atom, a straight- or branched-chain alkyl radical containing 1 to 10 carbon atoms, or an alkoxyalkyl group of the formula —(CH$_2$)$_n$—OR in which R represents a straight- or branched-chain alkyl radical containing 1 to 8 carbon atoms and n represents 1 or 2, and acid addition salts thereof.

The compounds of general formula I can exist in (R) and (S) forms and the invention includes both such forms and mixtures thereof.

According to a feature of the present invention, the indole derivatives of general formula I are prepared by the process which comprises the cyclisation of an indoline derivative of the general formula:

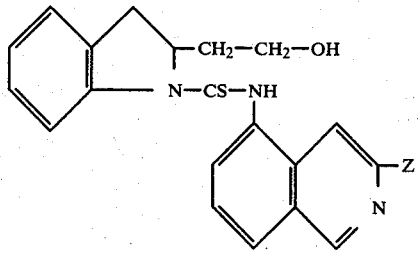

wherein Z is as hereinbefore defined.

The reaction is generally carried out in the presence of trifluoromethanesulphonic anhydride or methanesulphonyl chloride is an organic solvent, such as pyridine, at a temperature between 10° and 40° C.

The indoline derivatives of general formula II can be obtained by reacting an isothiocyanate of the general formula:

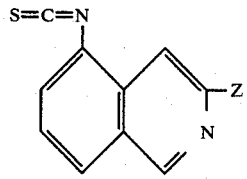

(wherein Z is as hereinbefore defined) with 2-(2-hydroxyethyl)indoline of the formula:

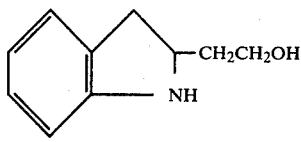

The reaction is generally carried out in an organic solvent such as an alcohol, e.g. ethanol, at a temperature between 20° and 50°1 C.

2-(2-Hydroxyethyl)indoline can be obtained by reducing 2-(2-hydroxyethyl)indole. The reduction is generally effected by means of sodium cyanoborohydride in acetic acid at a temperature between 10° and 30° C.

2-(2-Hydroxyethyl)indole can be prepared by the method described by T. Sakan et al., Tetrahedron Letters, 4925 (1968).

The isothiocyanates of general formula III can be obtained by reacting carbon disulphide with an amide of the general formula:

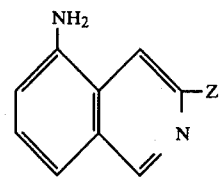

(wherein Z is as hereinbefore defined), the reaction being carried out under the conditions described in the specification of Belgian Pat. No. 863083 or U.S. Pat. No. 4,153,698.

5-Isothiocyanatoisoquinoline, i.e. the compound of general formula III wherein Z represents a hydrogen atom, can also be prepared from 5-aminoisoquinoline in accordance with the method described in the specification of British Pat. No. 1503091 or U.S. Pat. No. 4,064,247.

The 5-aminoisoquinolines of general formula V can be obtained from the corresponding isoquinolines by applying the method described by N. P. Buu-Hoï et al., J. Chem. Soc., 3924 (1964).

The 3-alkylisoquinolines can be prepared in accordance with the method described by J. Murakoshi et al., Yakugaku Zasshi, 79, 1578 (1959), or in accordance with the method described by F. Damerow, Ber., 27, 2232 (1894).

The 3-alkoxyalkylisoquinolines of the general formula:

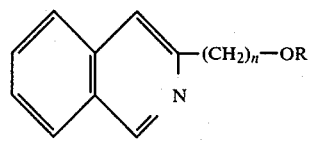

(wherein R and n are as hereinbefore defined) can be prepared by reacting a corresponding alkali metal alkoxide with a hydrohalide of a 3-halogenoalkylisoquinoline of the general formula:

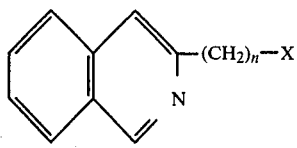

wherein n is as hereinbefore defined and X represents a chlorine or bromine atom. The reaction is generally carried out in solution in the corresponding alcohol R-OH (wherein R is as hereinbefore defined) at a temperature between 20° C. and the reflux temperature of the reaction mixture.

The hydrohalides of the 3-halogenoalkylisoquinolines of general formula VII can be prepared by halogenating a 3-hydroxyalkylisoquinoline of the general formula:

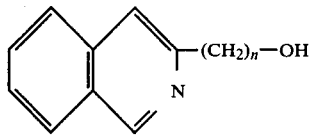

wherein n is as hereinbefore defined.

Chlorination is generally carried out by the action of thionyl chloride at a temperature between 25° C. and the reflux temperature of the reaction mixture.

Bromination is generally carried out by reaction of a concentrated aqueous solution of hydrobromic acid at a temperature between 50° C. and the reflux temperature of the reaction mixture.

3-Hydroxymethylisoquinoline can be prepared in accordance with the method described by B. R. Brown et al., J. Chem. Soc., 1145 (1951).

3-(2-Hydroxyethyl)isoquinoline can be prepared in accordance with the method described in Japanese Patent Publication 53/127483 (Derwent CPI 90295 A).

The isoquinoline derivatives of general formula VI wherein n represents 2 can also be obtained by hydrogenating an enol ether of the general formula:

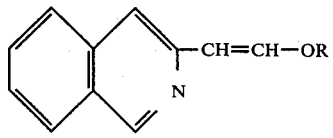

wherein R is as hereinbefore defined. The hydrogenation is generally carried out in the presence of palladium-on-charcoal as catalyst in an organic solvent, such as an alcohol (e.g. methanol or ethanol), at a temperature of about 20° C. under a pressure of about 15 atmospheres.

The enol ethers of general formula IX can be prepared by means of a Wittig reaction by condensing a phosphorane of the general formula:

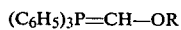

(C$_6$H$_5$)$_3$P=CH—OR    X (wherein R is as hereinbefore defined) with 3-formylisoquinoline, under the conditions described by A. Maercker, Organic Reactions, 14, 270 (1965).

3-Formylisoquinoline can be obtained in accordance with the method described by J. Teague, J. Amer. Chem. Soc., 73, 688 (1951).

The phosphoranes of general formula X can be prepared by treating the corresponding phosphonium bromide or chloride with a base, for example treatment with sodium methoxide in methanol or treatment with butyllithium in diethyl ether or tetrahydrofuran.

According to a further feature of the present invention, the indole derivatives of general formula I are prepared by the process which comprises the reaction of a 5-aminoisoquinoline of general formula V (wherein Z is as hereinbefore defined) with a salt of the general formula:

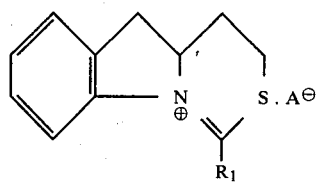

wherein R$_1$ represents a chlorine atom, an alkylthio radical containing 1 to 4 carbon atoms (preferably methylthio), or a benzylthio radical, and A$^\ominus$ represents an anion.

When R$_1$ represents a chlorine atom, A$^\ominus$ represents a chloride ion. When R$_1$ represents an alkylthio or benzylthio radical, A$^\ominus$ represents an iodide, sulphate, tetrafluoroborate or fluorosulphonate ion.

When R$_1$ represents a chlorine atom and A$^\ominus$ represents a chloride ion, the reaction is preferably carried out in an organic solvent, such as acetonitrile, in the presence of an alkaline condensing agent, such as triethylamine, at a temperature of about 20° C.

When R$_1$ represents an alkylthio or benzylthio radical and A$^\ominus$ represents an iodide, sulphate, tetrafluoroborate or fluorosulphonate ion, the reaction is preferably carried out in a basic organic solvent, such as pyridine, at a temperature between 30° and 50° C.

The salt of general formula XI wherein R$_1$ represents a chlorine atom and A$^\ominus$ represents a chloride ion can be obtained by the reaction of a chlorinating agent, such as phosgene, phosphorus pentachloride, thionyl chloride or oxalyl chloride, with [1,3-thiazino][3,4-a]indoline-4-thione of the formula:

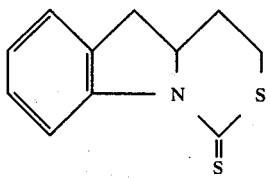

The reaction is generally carried out in an organic solvent or in a mixture of organic solvents, such as a mixture of toluene and tetrahydrofuran, at a temperature between 0° and 70° C.

The salts of general formula XI wherein R$_1$ represents an alkylthio or benzylthio radical and A$^\ominus$ represents an iodide, sulphate, tetrafluoroborate or fluorosulphonate ion, can be obtained by the action of a reactive ester of the general formula:

R$_2$—A$_1$    XIII (wherein R$_2$ represents an alkyl radical containing 1 to 4 carbon atoms or a benzyl radical, and A$_1$ represents the residue of a reactive ester such as an iodine atom or an alkoxysulphonyloxy radical), or by the action of triethyloxonium tetrafluoroborate or methyl fluorosulphonate, on the compound of formula XII. The reaction is generally carried out, optionally in the presence of an organic solvent such as methylene chloride, chloroform or dichloroethane, at a temperature of about 20° C.

[1,3-Thiazino][3,4-a]indoline-4-thione can be prepared by reacting 2-(2-hydroxethyl)indoline successively with carbon disulphide in the presence of a base and then with methanesulphonyl chloride or tosyl chloride, followed by cyclisation of the resulting intermediate obtained.

The reaction with carbon disulphide is generally carried out in the presence of a base such as a tertiary amine, e.g. triethylamine.

The successive reaction with carbon disulphide and then with methanesulphonyl chloride or tosyl chloride is advantageously carried out in an organic solvent, such as pyridine, at a temperature between −10° and 20° C.

The cyclisation of the intermediate is generally carried out by heating in an organic solvent, such as dimethylformamide or in a mixture or organic solvents (for example dimethylformamide and pyridine), at a temperature between 50° and 100° C. It is not necessary to isolate the intermediate in order to perform this cyclisation.

The indole derivatives of general formula I may be converted by known methods into acid addition salts. (By the term "known methods" is meant methods heretofore used or described in the chemical literature). The acid addition salts may be obtained by reacting the indole derivatives with acids in appropriate solvents. As organic solvents there may be used alcohols, ketones, ethers or chlorinated hydrocarbons. The salt which is formed is precipitated, if necessary after concentration of the solution, and is isolated by filtration or decantation.

The indole derivatives of general formula I and/or their acid addition salts can optionally be purified by physical methods such as crystallisation or chromatography.

The indole derivatives of general formula I possess useful pharmacological properties, in particular an analgesic agents. Some of them are also active as anti-inflammatory and antipyretic agents.

The analogesic activity manifests itself in mice at doses of between 2 and 30 mg/kg animal body weight, administered orally, using the technique of Siegmund et al., Proc. Soc. Exp. Biol. Med., 95, 729 (1957).

The anti-inflammatory activity of some of the products manifests itself in rats at doses of between 20 and 200 mg/kg animal body weight, administered orally, using the technique of K. F. Benitz and L. M. Hall, Arch. Int. Pharmacodyn., 144, 185 (1963).

The antipyretic activity of some of the products manifests itself in rats at doses of between 0.4 and 10 mg/kg animal body weight, administered orally, using the technique of J. J. Loux et al., Toxicol. Appl. Pharmacol., 22, 674 (1972).

Furthermore, the indole derivatives of the present invention are of very low toxicity. Their acute toxicity in mice, expressed as their $LD_{50}$, is more than 900 mg/kg animal body weight, administered orally.

Of particular value are the indole derivatives of general formula I wherein Z represents a hydrogen atom, a methyl or ethyl radical, or a group of the formula —$CH_2$—OR′ wherein R′ represents a methyl or ethyl radical, and more especially 4-[(3-methylisoquinol-5-yl)imino]-1,2,10,10a-tetrahydro[1,3-thiazino][3,4-a]indole, 4-[(3-ethoxymethylisoquinol-5-yl)imino]-1,2,10,10a-tetrahydro[1,3-thiazino][3,4-a]indole and 4-(isoquinol-5-ylimino)-1,2,10,10a-tetrahydro[1,3-thiazino][3,4-a]indole, and their acid addition salts. Preferred compounds are those in the (RS) form.

For therapeutic purposes the indole derivatives of general formula I are employed as such or in the form of pharmaceutically acceptable acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of the new indole derivatives of the present invention.

EXAMPLE 1

Trifluoromethanesulphonic anhydride (23.2 cc) is added dropwise, at a temperature of about 20° C., to a solution of (RS)-2-(2-hydroxyethyl)-N-(3-methylisoquinol-5-yl)indoline-1-carbothioamide (51 g) in pyridine (300 cc). An intense red solution is formed and this is stirred for 24 hours at 20° C. It is then concentrated to dryness at 40° C. under reduced pressure (20 mm Hg). The residue is taken up in a mixture of methylene chloride (300 cc) and a 10% aqueous solution of sodium carbonate (300 cc). The organic phase is decanted, washed with water (2×50 cc), dried over magnesium sulphate and filtered and the filtrate is evaporated to dryness at 40° C. under reduced pressure (20 mm Hg). The residue is recrystallised from ethanol (500 cc) and then from propanol (300 cc). After drying, (RS)-4-[(3-methylisoquinol-5-yl)imino]-1,2,10,10a-tetrahydro[1,3-thiazino][3,4-a]indole (20.2 g), a pale pink solid melting at 190° C., is obtained.

(RS)-2-(2-Hydroxyethyl)-N-(3-methylisoquinol-5-yl)indoline-1-carbothioamide can be prepared in the following manner:

2-(2-Hydroxyethyl)indoline (43 g) and 5-isothiocyanato-3-methylisoquinoline (52 g) are dissolved in ethanol (800 cc). The solution, which is kept for 24 hours at a temperature of about 20° C., deposits a solid which is isolated by filtration, washed with ethanol (3×50 cc) and dried. (RS)-2-(2-Hydroxyethyl)-N-(3-methylisoquinol-5-yl)indoline-1-carbothioamide (51 g), a white solid, is obtained.

2-(2-Hydroxyethyl)indoline can be prepared in the following manner:

Sodium cyanoborohydride (63 g) is added in portions to a stirred solution of 2-(2-hydroxyethyl)indole (43 g) in acetic acid (750 cc), whilst cooling the reaction mixture with a bath of cold water so as not to exceed 20° C. The mixture is stirred for 24 hours at this temperature. It is then concentrated to about 100 cc at 50° C. under reduced pressure (20 mm Hg). The residue is taken up in a mixture of water and ice (500 cc), the resulting mixture is rendered alkaline to pH 10 with an aqueous solution of sodium hydroxide and extraction is carried out with diethyl ether (3×300 cc). The organic extracts are combined, washed with water (50 cc), dried over magnesium sulphate and filtered and the filtrate is evaporated to dryness at 40° C. under reduced pressure (20 mm Hg). 2-(2-Hydroxyethyl)indoline (43 g) is obtained in the form of a yellow oil (mass spectrum m/e=163).

2-(2-Hydroxyethyl)indole can be prepared by the method described by T. Sakan et al., Tetrahedron Letters, 4925 (1968).

5-Isothiocyanato-3-methylisoquinoline can be prepared in accordance with the method described in the specification of Belgian Patent 863083 or United States Patent 4153698.

EXAMPLE 2

By following the procedure of Example 1 but using (RS)-2-(2-hydroxyethyl)-N-(isoquinol-5-yl)indoline-1-carbothioamide (15.4 g) and trifluoromethanesulphonic anhydride (17 g), (RS)-4-(isoquinol-5-ylimino)-1,2,10,10a-tetrahydro[1,3-thiazino][3,4-a]indole (4.6 g), a beige solid melting at 208° C. after recrystallisation from isopropanol, is obtained.

(RS)-2-(2-Hydroxyethyl)-N-(isoquinol-5-yl)indoline-1-carbothioamide can be prepared in a manner similar to that described in Example 1 for the homologous compound using 2-(2-hydroxyethyl)indoline (10.5 g) and 5-isothiocyanatoisoquinoline (11.9 g) as starting materials. A product (15.4 g), a white solid melting at 181° C., is obtained.

5-Isothiocyanatoisoquinoline can be prepared in accordance with the method described in British Pat. No. 1503091.

EXAMPLE 3

By following the procedure of Example 1 but using (RS)-2-(2-hydroxyethyl)-N-(3-ethoxymethylisoquinol-5-yl)indoline-1-carbothioamide (11 g) and trifluoromethanesulphonic anhydride (7.6 g), (RS)-4-[(3-ethoxymethylisoquinol-5-yl)imino]-1,2,10,10a-tetrahydro[1,3-thiazino][3,4-a]indole (6.9 g), melting at 142° C. after recrystallization from ethanol, is obtained.

(RS)-2-(2-Hydroxyethyl)-N-(3-ethoxymethylisoquinol-5-yl)indoline-1-carbothioamide can be prepared in a manner similar to that described in Example 1 for the homologous compound using 2-(2-hydroxyethyl)indoline (9.8 g) and 3-ethoxymethyl-5-isothiocyanatoisoquinoline (14.7 g) as starting materials. A product (11.1 g), melting at 152° C., is obtained.

3-Ethoxymethyl-5-isothiocyanatoisoquinoline can be prepared in the following manner:

A solution of carbon disulphide (16 cc) and triethylamine (4.5 cc) in pyridine (20 cc) is cooled to −10° C. A solution of 5-amino-3-ethoxymethylisoquinoline (6.5 g) in pyridine (20 cc) is added dropwise in the course of 5 minutes. The mixture is stirred for 3 hours at −10° C. and a solution of dicyclohexylcarbodiimide (6.6 g) in pyridine (20 cc) is then added. Stirring is continued, whilst leaving the reaction mixture to return to a temperature of about 20° C. The mixture is stirred for 24 hours at this temperature and then concentrated to dryness at 50° C. under reduced pressure (20 mm Hg). The residue is taken up in methylene chloride (25 cc). An insoluble material is filtered off and the filtrate is evaporated to dryness at 40° C. under reduced pressure (20 mm Hg). The residue is taken up in diisopropyl ether (200 cc). The isoluble yellow solid is isolated by filtration, washed with diisopropyl ether (20 cc) and dried. 3-Ethoxymethyl-5-isothiocyanatoisoquinoline (7 g), melting at 66° C., is obtained.

5-Amino-3-ethoxymethylisoquinoline can be prepared in the following manner:

A catalyst (3% palladium-on-charcoal; 3.5 g) is added to a solution of 3-ethoxymethyl-5-nitroisoquinoline (24 g) in ethanol (350 cc). A stream of hydrogen is bubbled through for 4 hours, whilst keeping the temperature at about 25° C. with the aid of a bath of cold water. The suspension is filtered and the filtrate is evaporated to dryness at 50° C. under reduced pressure (20 mm Hg). The residue is recrystallised from diisopropyl ether (200 cc). 5-Amino-3-ethoxymethylisoquinoline (16.5 g), melting at 95° C., is obtained.

3-Ethoxymethyl-5-nitroisoquinoline can be prepared in the following manner:

3-Ethoxymethylisoquinoline (31 g) is dissolved in 95% sulphuric acid (density 1.83; 100 cc). The solution is cooled to 0° C. and a mixture of 95% sulphuric acid (density 1.83; 35 cc) and 70% nitric acid (density 1.42; 10.2 cc) is added dropwise in the course of 30 minutes so as not to exceed 10° C. Stirring is continued for 16 hours whilst allowing the temperature to return to about 20° C. The mixture is then poured into a mixture of ice and water (1 liter), and an ammonia solution containing 20% of $NH_3$ (density 0.9) is added, without exceeding 30° C., until a pH of about 10 is obtained. The yellow suspension is extracted with methylene chloride (4×200 cc). The organic extracts are combined, washed with water (2×50 cc), dried over magnesium sulphate and filtered and the filtrate is evaporated to dryness at 40° C. under reduced pressure (20 mm Hg). 3-Ethoxymethyl-5-nitroisoquinoline (24 g), melting at 54° C., is obtained.

3-Ethoxymethylisoquinoline can be prepared in the following manner:

A mixture of 3-chloromethylisoquinoline hydrochloride (40 g) and sodium ethoxide (40 g) in ethanol (700 cc) is heated under reflux for 8 hours. After cooling to 20° C., the mixture is filtered and the filtrate is evaporated to dryness at 50° C. under reduced pressure (20 mm Hg). The residue is taken up in methylene chloride (500 cc), the mixture is washed with water (3×100 cc), the organic phase is dried over magnesium sulphate and filtered and the filtrate is evaporated to dryness at 40° C. under reduced pressure (20 mm Hg). The oily residue is distilled at 110°–114° C. under a pressure of 0.6 mm Hg. 3-Ethoxymethylisoquinoline (31 g), a colourless oil, is obtained.

3-Chloromethylisoquinoline hydrochloride can be prepared in the following manner:

3-Hydroxymethylisoquinoline (110 g) is added to thionyl chloride (130 cc), whilst cooling so as to keep the temperature between 25° and 30° C. The reaction mixture is then heated to the reflux temperature at a rate which is such that the evolution of gas is not excessive. The mixture is heated under reflux for 90 minutes (until the evolution of gas ceases), and then for a further 30 minutes. It is then cooled to 5° C. with ice, the slurry formed is filtered and the solid is washed with diethyl ether. 3-Chloromethylisoquinoline hydrochloride (136 g), melting at 202° C., is obtained.

3-Hydroxymethylisoquinoline can be prepared by the method described by B. R. Brown et al., J. Chem. Soc., 1145 (1951).

EXAMPLE 4

(RS)-4-Methylthio-1,2,10,10a-tetrahydro[1,3-thiazino][3,4-a]indolinium iodide (3.6 g) is added to a solution of 5-amino-3-ethoxymethylisoquinoline (2 g) in pyridine (100 cc) and the mixture is stirred for 80 hours at 20° C. It is then concentrated to dryness at 60° C. under reduced pressure (20 mm Hg). The residue is dissolved in methylene chloride (200 cc), the solution is washed with water (2×50 cc), dried over magnesium sulphate and filtered and the filtrate is concentrated to dryness at 40° C. under reduced pressure (20 mm Hg). The residue is recrystallised from ethanol. (RS)-4-[(3-Ethoxymethylisoquinol-5-yl]-1,2,10,10a-tetrahydro[1,3-thiazino][3,4-a]indole (2.7 g), melting at 142° C., is obtained.

(RS)-4-Methylthio-1,2,10,10a-tetrahydro[1,3-thiazino][3,4-a]indolinium iodide can be obtained in the following manner:

[1,3-Thiazino][3,4-a]indoline-4-thione (2.2 g) and methyl iodide (30 cc) are mixed. The resulting suspension is stirred for 4 hours at 20° C. It is then concentrated to dryness at 20° C. under reduced pressure (20 mm Hg). A pale yellow solid product (3.6 g) is obtained.

[1,3-Thiazino][3,4-a]indoline-4-thione can be obtained in the following manner: 2-(2-Hydroxyethyl)indoline (6 g) is dissolved in pyridine (50 cc). The solution is cooled to −10° C. Carbon disulphide (6 cc) is added, followed by triethylamine (11.2 cc). The mixture is stirred for 20 hours at −10° C. Methanesulphonyl chloride (12.8 cc) is then added and the mixture is stirred for 3 hours at −10° C. Dimethylformamide (200 cc) is added and the mixture is concentrated to dryness at 80° C. under reduced pressure (20 mm Hg). The residue is dissolved in methylene chloride (100 cc) and the solution is washed with water (2×50 cc), dried over magnesium sulphate and filtered and the filtrate is concentrated to dryness at 40° C. under reduced pressure (20 mm Hg). The residue is chromatographed on a column of diameter 1 cm, containing silica (200 g) in methylene chloride. Elution is carried out with this solvent, 50 cc fractions being collected. Fractions 6 to 12 are combined and concentrated to dryness at 40° C. under reduced pressure (20 mm Hg). A product (2.2 g), melting at 135° C., is obtained.

The present invention includes within its scope pharmaceutical compositions comprising, as active ingredient, at least one of the compounds of general formula I, or a non-toxic acid addition salt thereof, in association with one or more compatible pharmaceutically acceptable carriers or adjuvants. The invention includes especially such preparations made up for oral, parenteral, rectal or topical administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspension, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The compositions for topical application are, in particular, creams or ointments.

The pharmaceutical compositions according to the invention are particularly useful in human therapy for their analogesic, anti-inflammatory and antipyretic action. They are particularly indicated for the treatment of acute and chronic pains, rheumatic and traumatic algias, dental, neurological and visceral pains, various algias (pains experienced by cancer patients), inflammatory diseases (ankylosing spondylarthritis, acute articular rheumatism and arthrosis), and febrile conditions.

In human therapy, the doses depend on the desired effect and the duration of the treatment; for an adult, they are generally between 100 and 2000 mg per day.

In general, the physician will decide the posology considered most appropriate, taking into account the age, weight and other factors intrinsic to the patient being treated.

The following Examples illustrate pharmaceutical compositions according to the invention.

EXAMPLE 5

Tablets containing 100 mg doses of active product and having the following composition are prepared in accordance with the usual technique:

| | |
|---|---|
| (RS)-4-[(3-methylisoquinol-5-yl)imino]-1,2,10,10a-tetrahydro[1,3-thiazino]-[3,4-a]indole | 0.100 g |
| starch | 0.110 g |
| precipitated silica | 0.035 g |
| magnesium stearate | 0.005 g |

EXAMPLE 6

Tablets containing 100 mg doses of active product and having the following composition are prepared in accordance with the usual technique:

| | |
|---|---|
| (RS)-4-[(3-ethoxymethylisoquinol-5-yl)-imino]-1,2,10,10a-tetrahydro[1,3-thiazino]-[3,4-a]indole | 0.100 g |
| starch | 0.110 g |
| precipitated silica | 0.035 g |
| magnesium stearate | 0.005 g |

We claim:

1. An indole derivative of the formula:

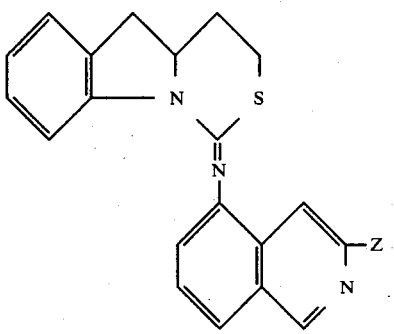

wherein Z represents hydrogen, alkyl of 1 through 10 carbon atoms, or alkoxyalkyl of the formula —(CH$_2$)$_n$—OR in which R represents alkyl of 1 through 8 carbon atoms and n represents 1 or 2, and its non-toxic pharmaceutically acceptable acid addition salts.

2. An indole derivative according to claim 1 wherein Z represents hydrogen, methyl or ethyl, or a group —CH$_2$—OR' in which R' represents methyl or ethyl and its non-toxic pharmaceutically acceptable acid addition salts.

3. The indole derivative according to claim 1 which is 4-[(3-methylisoquinol-5-yl)imino]-1,2,10,10a-tetrahydro[1,3-thiazino][3,4-a]indole and its non-toxic pharmaceutically acceptable acid addition salts.

4. The indole derivative according to claim 1 which is 4-[(3-ethoxymethylisoquinol-5-yl)imino]-1,2,10,10a-tetrahydro[1,3-thiazino][3,4-a]indole and its non-toxic pharmaceutically acceptable acid addition salts.

5. The indole derivative according to claim 1 which is 4-(isoquinol-5-ylimino)-1,2,10,10a-tetrahydro[1,3-thiazino][3,4-a]indole and its non-toxic pharmaceutically acceptable acid addition salts.

6. An indole derivative according to any one of claims 1 to 5 in the (RS) form.

7. A pharmaceutical composition useful as an analgesic agent or—when appropriate —as an antiinflammatory or antipyretic agent which comprises as active ingredient an effective amount of an indole derivative of the formula depicted in claim 1, wherein Z is as defined in claim 1, or a non-toxic pharmaceutically acceptable acid addition salt thereof, in association with a significant amount of a compatible pharmaceutically acceptable carrier.

* * * * *